US012678455B2

(12) United States Patent
Meyer

(10) Patent No.: US 12,678,455 B2
(45) Date of Patent: Jul. 14, 2026

(54) INHIBITION OF CRYSTALLIZATION AND/OR BIOFILM FORMATION ON AN INDWELLING URINARY CATHETER

(71) Applicant: Prosalix AG, Basel (CH)

(72) Inventor: Bruno Meyer, Grellingen (CH)

(73) Assignee: PROSALIX AG, Basel (CH)

( * ) Notice: Subject to any disclaimer, the term of this patent is extended or adjusted under 35 U.S.C. 154(b) by 259 days.

(21) Appl. No.: 18/556,173

(22) PCT Filed: Apr. 20, 2022

(86) PCT No.: PCT/EP2022/060468
§ 371 (c)(1),
(2) Date: Oct. 19, 2023

(87) PCT Pub. No.: WO2022/223650
PCT Pub. Date: Oct. 27, 2022

(65) Prior Publication Data

US 2024/0216423 A1 Jul. 4, 2024

(30) Foreign Application Priority Data

Apr. 21, 2021 (EP) .................................... 21169737

(51) Int. Cl.

| | |
|---|---|
| ***A61K 33/00*** | (2006.01) |
| ***A61K 33/06*** | (2006.01) |
| ***A61P 31/04*** | (2006.01) |

(52) U.S. Cl.
CPC .............. *A61K 33/06* (2013.01); *A61K 33/00* (2013.01); *A61P 31/04* (2018.01)

(58) Field of Classification Search
None
See application file for complete search history.

(56) References Cited

U.S. PATENT DOCUMENTS

2020/0316002 A1 10/2020 Cuñe

FOREIGN PATENT DOCUMENTS

| | | |
|---|---|---|
| KR | 2014-0126466 | 10/2014 |
| WO | WO 2016/159898 | 10/2016 |

(Continued)

OTHER PUBLICATIONS

Stickler et al. (Strategies for the control of catheter encrustation; International Journal of Antimicrobial Agents 19 (2002): 499-506)). (Year: 2002).*

(Continued)

*Primary Examiner* — Ernst V Arnold
(74) *Attorney, Agent, or Firm* — Buscher Patent PLLC

(57) ABSTRACT

The present invention relates to a composition for use in inhibition of crystallization and/or biofilm formation on an indwelling urinary catheter. The composition of the present invention comprises magnesium ions, potassium ions and citrate ions. Preferably the composition of the present invention consists of 74.2 weight % of tripotassium citrate monohydrate and of 25.8 weight % of anhydrous trimagnesium citrate. Its administration reduces the risk of obstruction of a urinary catheter, reduces the risk of a catheter-associated urinary tract infection, reduces the risk of bladder stone formation, reduces the risk of an injury of urethra mucosa as a result of exchange of the indwelling urinary catheter, and allows application of an indwelling urinary catheter for a prolonged period of time.

17 Claims, 2 Drawing Sheets

(56) References Cited

FOREIGN PATENT DOCUMENTS

| | | | | |
|---|---|---|---|---|
| WO | WO 2019/201707 | | 10/2019 | |
| WO | WO-2019201707 A1 | * | 10/2019 | ............... A61K 9/08 |
| WO | WO 2021/136765 | | 7/2021 | |

OTHER PUBLICATIONS

D. J. Stickler et al., *Journal of Medical Microbiology* (2006), 55, pp. 489-494.

Y.H. Wang et al., *British Journal of Urology* (1994), 74, pp. 409-415.

* cited by examiner

INHIBITION OF CRYSTALLIZATION AND/OR BIOFILM FORMATION ON AN INDWELLING URINARY CATHETER

FIELD OF THE INVENTION

The present invention relates to a composition for use in inhibition of crystallization and/or biofilm formation on indwelling urinary catheter. The composition of the present invention comprises magnesium (preferably in the form of ions), potassium (preferably in the form of ions) and citrate (preferably in the form of ions) and its administration reduces the risk of obstruction of a urinary catheter, reduces the risk of a catheter-associated urinary tract infection, reduces the risk of bladder stone formation, reduces the risk of an injury of urethra mucosa as a result of exchange of the indwelling urinary catheter, and allows application of the urinary catheter for a prolonged period of time.

BACKGROUND OF THE INVENTION

Catheters are one of the most commonly used medical devices in the world and, depending on the mode of use and period of catheterization, can be characterized as either indwelling or intermittent catheters. When problems arise in the lower urinary tract such as nerve damage or muscle atrophy leading to incontinence, or by prostate enlargement or urethral stricture resulting in urinary retention, the use of urinary catheter in a patient becomes a necessity. A urinary catheter is typically a long tube that is inserted into urethra until the urine begins to flow. An indwelling urinary catheter, for example inserted through the urethra, is a type of catheter that is left in place, for a longer period of time. Two other types of catheters that are commonly used are suprapubic catheters and pigtail catheters.

In the clinical practice, formation of biofilm and/or formation of crystals (also referred to herein as crystallization) on indwelling urinary catheters can seriously complicate the care of patients undergoing long-term bladder catheterization. As discussed herein, a biofilm is defined as microorganisms bound to a surface of each other with the presence of an extracellular matrix, preferably comprising secreted products of the organisms and/or components of the microorganisms themselves and/or other components (e.g. proteins). The cells within the biofilm may be irreversibly bound to the surface and to each other via secreted, adhesive substances. The biofilm may contain one microorganism species or several microorganism species, including bacteria (both Gram-negative and Gram-positive) and yeasts. It is noted that while patients who are catheterized short term (not more than 7 days) experience the biofilm formation on the urinary catheter in 10% to 50% of the cases, practically all patients who are catheterized over a long term (more than 28 days) develop biofilm on the indwelling urinary catheter.

The advantages for a microorganism to be within a biofilm include antimicrobial resistance, protection from physical forces, and safety from phagocytosis by immune cells. The ability of biofilms to resist antimicrobial agents is particularly worrying, as mechanisms of resistance, such as genes encoding for antimicrobial resistance, can be transferred throughout the community and even further afield as microorganisms leave the biofilm to spread and multiply. It is noted that preventing or inhibiting biofilm formation may therefore be a more efficient biofilm management strategy than its removal through, for example, use of an antimicrobial agent, once it is formed.

When functioning normally, the lower urinary tract flushes out the urethra as the bladder empties, thus preventing the movement of bacterial from the periurethral skin into the urethra and then into the bladder. It is noted that the long-held idea that the bladder and urine itself are sterile is a misconception, and it is known to the skilled person that body's intricate microbiome is also present in the bladder and urine. These bacteria include *Corynebacterium* species in male urinary tracts and *Lactobacillus* species in female urinary tracts. The cellular structure of the bladder and the regular emptying of its contents usually prevent bacteria from multiplying to dangerous levels or adhering to the surrounding mucosa. When a foreign object like a catheter is introduced, excessive bacterial contamination may occur.

Biofilm formation may be accompanied by crystallization on the surface of a urinary catheter, in particular an indwelling urinary catheter. Without wishing to be bound to the theory, it is noted that generation of alkaline urine by the bacterial urease is thought to cause calcium and magnesium phosphates to precipitate from urine and accumulate in the catheter biofilm. Eventually, this may lead to blocking of urine flow from the bladder. It is noted that while calcium and magnesium are found both in the crystalline precipitates on indwelling urinary catheters, calcium has been shown to play a major role in this process.

Thus, it may be so construed that presence of certain bacteria in the urinary tract leads to crystallization. In certain patients however, the crystallization in the urinary catheter may also occur due to metabolic dysfunction. Crystallization as referred to herein may also manifest itself in formation of bladder stones, which have also been historically referred to as infection stones.

A biofilm and/or crystallization can also influence and change aspects of the surrounding environment, in particular affect urine flow through a catheter. Indwelling catheters upon biofilm formation and crystallization may become blocked, leading to urine retention that is not just painful for the patient but also constitutes a medical emergency. If upon biofilm formation and crystallization the catheter becomes blocked, it must be removed to avoid damaging the bladder, ureters, and kidneys; if the pressure builds to a high enough level in the bladder, ureteric reflux can occur where urine is forced backwards up into the ureters and into the kidneys. In some patients, catheter crystallization can be so extreme that removal of the catheter can require emergency surgery.

Citrate acts as a chelating agent for divalent metal ions, and as such it can keep calcium and magnesium in solution. Furthermore, citrate can be used to control pH of the urine and thus prevent precipitation and/or crystallization of calcium- and magnesium-containing salts. However, formulating citrate in a suitable form for administration to a subject/to a patient has been challenging to date.

Stickler et al (J. Med. Microbiol., 2006, 55, 489-494) disclose the model study wherein formation of the crystalline biofilm in the laboratory models of catheterized bladder infected with *P. mirabilis* exposed to urine containing citrate is followed.

Wang et al. (British Journal of Urology, 1994, 74, 409-415) demonstrated that oral intake of sodium and potassium citrate leads to decreased crystal growth and precipitation in urine.

SUMMARY OF THE INVENTION

It was the objective technical problem of the present invention to provide improved means for use in inhibition of crystallization and/or biofilm formation on an indwelling urinary catheter.

The objective technical problem is solved by the embodiments disclosed herein and as characterized by the claims.

The present inventors have surprisingly shown that the composition of the present invention comprising magnesium (preferably in the form of ions), potassium (preferably in the form of ions) and citrate (preferably in the form of ions) can effectively inhibit biofilm formation and/or crystallization on the indwelling urinary catheters. The present inventors have further surprisingly shown that the composition of the invention is well complied with by the patients, in particular by limiting the extent of side effects that administration of the composition may lead to.

The present invention will be summarized in the following embodiments.

In the first embodiment, the present invention relates to a composition comprising magnesium, potassium and citrate for use in inhibition of crystallization and/or biofilm formation on an indwelling urinary catheter. The administration of the composition to a subject is preferably to begin substantially at the same time as the catheterization of said subject.

In a particular embodiment, the present invention relates to a composition as described herein, wherein magnesium, potassium and citrate are present as ion(s). Thus, the present invention relates to a composition comprising magnesium ions, potassium ions and citrate ions for use in inhibition of crystallization and/or biofilm formation on indwelling urinary catheter.

In a particular embodiment, the present invention relates to the composition as described herein, wherein the molar ratio of potassium ions to magnesium ions in the composition is between 3.2:1 and 5.5:1.

In a further particular embodiment, the present invention relates to the composition as described herein, wherein the molar ratio of potassium ions to magnesium ions to citrate ions in the composition is about 4:1:2, preferably 4:1:2.

In again a further particular embodiment, the present invention relates to the composition as described herein, wherein the composition comprises trimagnesium citrate, preferably anhydrous trimagnesium citrate, and/or wherein the composition comprises tripotassium citrate, preferably tripotassium citrate monohydrate.

In a further particular embodiment, the present invention relates to the composition as described herein, wherein the tripotassium citrate monohydrate constitutes 70-80 weight % of the citrate salts in the composition, and wherein anhydrous trimagnesium citrate constitutes 20-30 weight % of the citrate salts in the composition.

In again a further particular embodiment, the present invention relates to the composition as described herein, wherein the tripotassium citrate monohydrate constitutes 74.2 weight % of the citrate salts in the composition, and wherein anhydrous trimagnesium citrate constitutes 25.8 weight % of the citrate salts in the composition.

In again a further particular embodiment, the present invention relates to the composition as described herein, wherein the composition consists of 74.2 weight % of tripotassium citrate monohydrate and of 25.8 weight % of anhydrous trimagnesium citrate.

In again a further particular embodiment, the present invention relates to the composition as described herein, wherein upon dissolution of the composition in water the pH is between 6.0 and 9.0.

In again a further particular embodiment, the present invention relates to the composition as described herein, wherein the composition is to be administered orally.

In again a further particular embodiment, the present invention relates to the composition as described herein, wherein the composition further comprises a pharmaceutically acceptable excipient.

In again a further particular embodiment, the present invention relates to the composition as described herein, wherein a single dose of the composition comprises between 10 and 30 mEq of citrates.

In again a further particular embodiment, the present invention relates to the composition as described herein, wherein a daily dose of the composition comprises between 10 and 60 mEq of citrates.

In again a further particular embodiment, the present invention relates to the composition as described herein, wherein administration of the composition reduces the risk of obstruction of an indwelling urinary catheter.

In again a further particular embodiment, the present invention relates to the composition as described herein, wherein administration of the composition allows application of the indwelling urinary catheter for a prolonged period of time.

In again a further particular embodiment, the present invention relates to the composition as described herein, wherein administration of the composition reduces the risk of a catheter-associated urinary tract infection.

In again a further particular embodiment, the present invention relates to the composition as described herein, wherein the inhibited crystallization and/or biofilm formation is caused by presence of *Proteus mirabilis, Proteus vulgaris*, and/or *Providentia rettgeri*, preferably of *Proteus mirabilis.*

In again a further particular embodiment, the present invention relates to the composition as described herein, wherein the inhibited biofilm formation is caused by presence of *Pseudomonas aeruginosa, Staphylococcus aureus, Klebsiella pneumoniae, Escherichia coli, Citrobacter* spp. and/or yeast, in particular *Candida albicans.*

In again a further particular embodiment, the present invention relates to the composition as described herein, wherein administration of the composition reduces the risk of bladder stone formation.

In again a further particular embodiment, the present invention relates to the composition as described herein, wherein the composition of the present invention is to be administered to a subject in a dose so that the concentration of citrate ions in urine of said subject reaches a concentration of at least 1 mmol/L, more preferably at least 2 mmol/L, even more preferably at least 3 mmol/L, even more preferably about 4 mmol/L, most preferably 4 mmol/L.

In again a further particular embodiment, the present invention relates to the composition as described herein, wherein administration of the composition reduces the risk of an injury of urethra mucosa as a result of exchange of the indwelling urinary catheter.

In another embodiment, the present invention relates to use of the composition as described herein for inhibition of crystallization and/or biofilm formation on an indwelling urinary catheter.

DETAILED DESCRIPTION OF THE INVENTION

Figure 1:
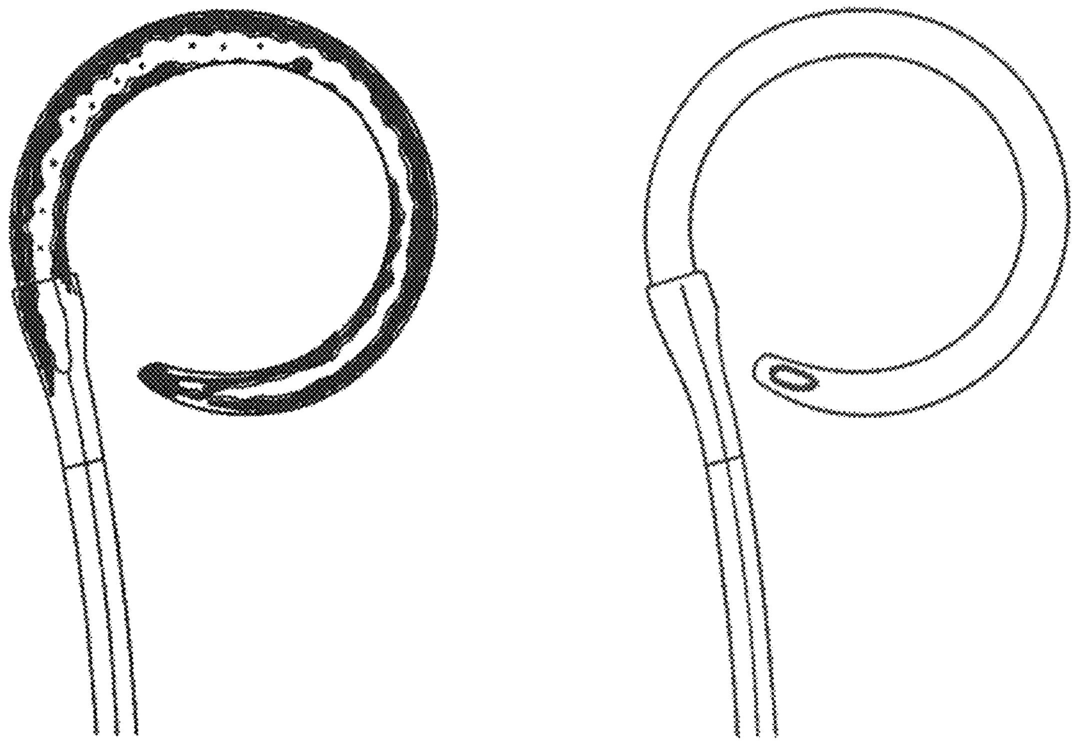
FIG. 1: Comparison of an indwelling urinary catheter blocked as a result of biofilm formation and crystallization (left) and a normal not blocked catheter (right).
Figure 2:
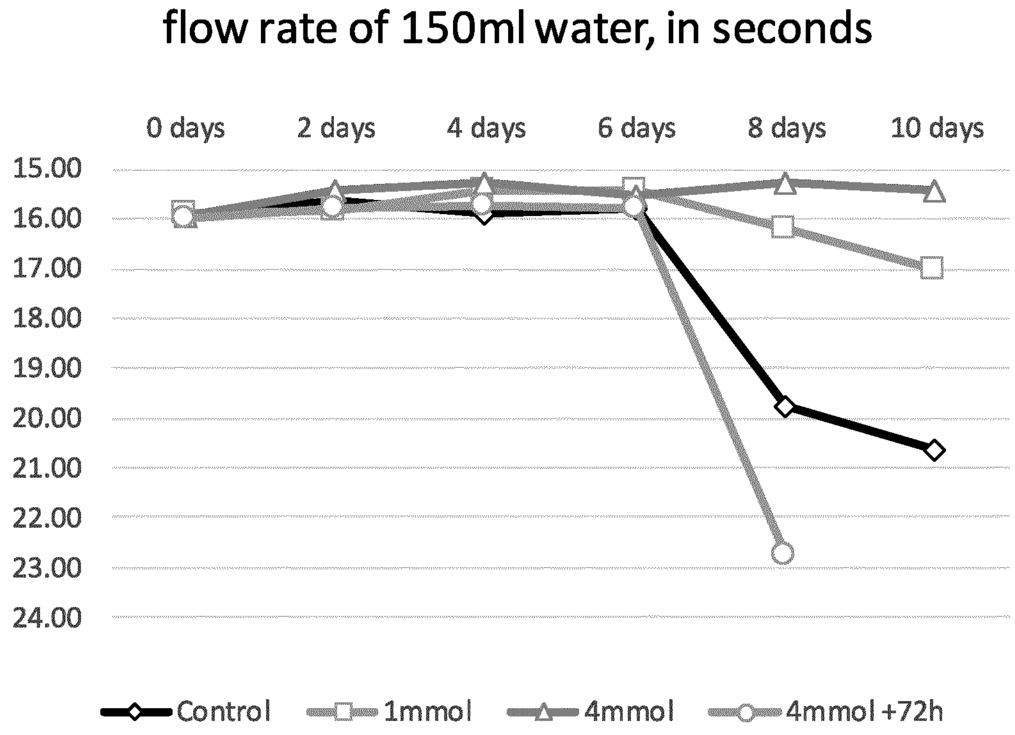
FIG. 2: Stenosis of bladder catheters due to urease-induced biofilm- and crystallization-formation with subsequent encrustation measured by throughflow rates and its inhibition by Pro24c (an in vitro-study).

The compositions for use of the invention will be described in the following. It is to be understood that all possible combinations of the features as described herein are also envisaged.

In the first embodiment, the present invention relates to a composition comprising magnesium, potassium and citrate for use in inhibition of crystallization and/or biofilm formation on an indwelling urinary catheter. Preferably, magnesium, potassium and/or citrate are present as ion(s). Thus, the present invention relates to a composition comprising magnesium ions, potassium ions and citrate ions for use in inhibition of crystallization and/or biofilm formation on an indwelling urinary catheter. As understood herein, the magnesium ions, also referred to as $Mg^{2+}$, are present within the composition of the present invention in a form of a salt. Further as understood herein, the potassium ions also referred to as $K^+$ are present within the composition of the present invention in a form of a salt. Further as understood herein, the citrate ions are present within the composition of the present invention in a form of a salt. The citrate ions, which term preferably refers to fully deprotonated for of citric acid, may be represented by the chemical formula:

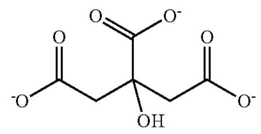

However, as it is apparent to the skilled person, all possible tautomeric forms of the citrate, in addition to the one depicted in the formula hereinabove, are also encompassed within the scope of the present invention. The skilled person is aware that citrate ions may exist in different protonation states, including fully deprotonated form as shown above, which may also be referred to as $citrate^{3-}$, as well as partially protonated forms $H\text{-}citrate^{2-}$ and $H_2\text{-}citrate^{-}$. As understood herein, unless provided otherwise, whenever reference to the citrate is made, a fully deprotonated form $citrate^{3-}$ is meant.

Preferably, the composition of the present invention is a solid composition. The solid composition comprising magnesium ions, potassium ions and citrate ions for use in inhibition of crystallization and/or biofilm formation on indwelling urinary catheter may be understood herein as a composition comprising salts made of magnesium ions, potassium ions and citrate ions, as defined herein. The definition of the composition of the present invention does not exclude presence of further ions, beyond magnesium ions, potassium ions and citrate ions. However, preferably the composition of the present invention substantially does not include further ions beyond magnesium ions, potassium ions and citrate ions. "Substantially" as understood herein, in particular in the context "substantially does not include further ions" is meant to be understood as "may include no more than 10% of further ions, preferably no more than 5% further ions". In other words, the composition of the present invention contains only salts made of ions selected from magnesium ions, potassium ions and citrate ions, the citrate ions preferably being the fully deprotonated form of citric ions.

The present inventors have surprisingly found that compositions characterized by certain molar ratios of magnesium ions to potassium ions are particularly useful when used use in inhibition of crystallization and/or biofilm formation on an indwelling urinary catheter. Therefore, in a particular embodiment, the present invention relates to the composition for use as described herein, wherein the molar ratio of potassium ions to magnesium ions in the composition is between 3.2:1 and 5.5:1. In a preferred embodiment, the molar ratio of potassium ions to magnesium ions in the composition is between 3.5:1 and 5.0:1. More preferably, the molar ratio of potassium ions to magnesium ions in the composition is between 3.8:1 and 4.5:1. Even more preferably, the molar ratio of potassium ions to magnesium ions in the composition is about 4:1, most preferably the molar ratio of potassium ions to magnesium ions in the composition is 4:1.

In a further preferred embodiment, as discussed herein, substantially no further ions are present in the composition beyond magnesium ions, potassium ions and citrate ions. Therefore, amount of citrate ions relative to the amount of potassium and magnesium ions, may be calculated by a skilled person assuming the charge neutrality of the composition of the present invention. Thus within the scope of the present invention, a particularly preferred is an embodiment, wherein the molar ratio of potassium ions to magnesium ions to citrate ions in the composition is about 4:1:2, preferably 4:1:2. In other words, particularly preferred is an embodiment, wherein the molar ratio of potassium ions to magnesium ions is about 4:1, wherein the molar ratio of potassium ions to citrate ions (preferably fully deprotonated) is about 2:1 (which may also be referred to as 4:2), and wherein the molar ration of magnesium ions to citrate ions (preferably fully deprotonated) is about 1:2. In a further even more preferred embodiment, the molar ratio of potassium ions to magnesium ions is 4:1, the molar ratio of potassium ions to citrate ions (preferably fully deprotonated) is 2:1 (which may also be referred to as 4:2), and the molar ration of magnesium ions to citrate ions (preferably fully deprotonated) is 1:2.

The composition of the present invention may comprise different salts, as long as it complies with the requirements as recited hereinabove.

Preferably, the composition of the present invention comprises trimagnesium citrate, which may also be referred to as $Mg_3citrate_2$, trimagnesium dicitrate, trimagnesium citrate, or magnesium citrate (3:2). Preferably, the trimagnesium citrate is present in the composition as an anhydrous trimagnesium citrate.

Preferably, the composition of the present invention comprises tripotassium citrate, which may also be referred to as $K_3citrate$. Further preferably, the tripotassium citrate, as referred to herein, is present in the composition in the form of a monohydrate, which may also be referred to as $K_3citrate \times H_2O$.

Preferably, the salts comprised in the composition as disclosed herein are to be provided as fulfilling the quality standards appropriate for the active pharmaceutical ingredient (API), which are known to the skilled person. Preferably, trimagnesium citrate, or anhydrous trimagnesium citrate, as used herein, shall refer to trimagnesium citrate that is provided as being of API-quality standards. Further preferably, tripotassium citrate monohydrate, as used herein, shall refer to tripotassium citrate monohydrate, that is provided as being of API-quality standards.

Preferably thus, the present invention relates to the composition as described herein, wherein the composition comprises trimagnesium citrate, preferably anhydrous trimagnesium citrate, and/or wherein the composition comprises tripotassium citrate, preferably tripotassium citrate monohydrate. More preferably, the present invention relates to the composition as described herein, wherein the composition comprises trimagnesium citrate, preferably anhydrous trimagnesium citrate, and tripotassium citrate, preferably tripotassium citrate monohydrate. Even more preferably, the present invention relates to a composition comprising anhydrous trimagnesium citrate and tripotassium citrate monohydrate. In a particularly preferred embodiment, the present invention relates to a composition consisting of anhydrous trimagnesium citrate and tripotassium citrate monohydrate. In other words, no other components are substantially present in the so defined composition of the present invention.

The present inventors have surprisingly found that compositions for use of the present invention comprising anhydrous trimagnesium citrate and tripotassium citrate monohydrate characterized by certain relationship of contents of both salts are particularly useful when used in inhibition of crystallization and/or biofilm formation on an indwelling urinary catheter. Thus, in a further particular embodiment, the present invention relates to the composition as described herein, wherein the tripotassium citrate monohydrate constitutes 70-80 weight % of the citrate salts in the composition, and wherein trimagnesium citrate constitutes 20-30 weight % of the citrate salts in the composition. The term “weight % of the citrate salts in the composition” refers preferably to a weight of one particular citrate salt in the composition (including any crystalline water present in the salt) to the total weight of all the citrate salts in the composition. As preferably the present invention relates to a composition consisting of anhydrous trimagnesium citrate and tripotassium citrate monohydrate, for the composition consisting of anhydrous trimagnesium citrate and tripotassium citrate monohydrate it is understood that both weight % of the citrate salts of the composition would refer to weight % of each component in the composition. Thus preferably, the weight % as given hereinabove preferably sum up to 100%.

In a preferred embodiment, the present invention relates to the composition as described herein, wherein the tripotassium citrate monohydrate constitutes 74.2 weight % of the citrate salts in the composition, and wherein anhydrous trimagnesium citrate constitutes 25.8 weight % of the citrate salts in the composition. As preferably the present invention relates to a composition consisting of anhydrous trimagnesium citrate and tripotassium citrate monohydrate. Thus, in again a preferred embodiment, the present invention relates to the composition as described herein, wherein the composition consists of 74.2 weight % of tripotassium citrate monohydrate and of 25.8% weight % of anhydrous trimagnesium citrate.

The preferred ratio of tripotassium citrate monohydrate and anhydrous trimagnesium citrate has been surprisingly found by the present inventors to allow for maximizing the possible administered dose of citrate, at the same time minimizing the risk of side effects resulting from administration of potassium ions (i.e. hyperkalaemia, cardiological complications, bitter or metallic taste leading to reduced compliance) and/or administration of magnesium ions (laxative effect at elevated doses). It is noted that said side effects will be discussed in the following.

The composition for use of the present invention is preferably to be prepared as a mixture of two salts, as discussed herein, which may be present in a form of a powder and/or a granulate. Preferably, the composition, which in certain embodiments is a solid composition, is to be packed in a waterproof sachet so that a subject, or a patient, may dissolve the content of the single sachet, corresponding to a single dose of the composition of the present invention, in water, promptly before administration. It is herein noted that while the solid form of the composition of the present invention is preferred, the liquid galenic forms comprising magnesium ions, potassium ions and citrate ions according to the present invention, as described hereinabove, are also encompassed by the present invention.

As understood herein, the single dose of the composition of the present invention, as long as the composition is provided in the solid form, should preferably be dissolved in the amount of water from 50 to 150 ml, more preferably in the amount of water of about 100 ml. It is noted that upon dissolution of the composition in water the pH is between 6.0 and 9.0.

It is noted that the powder of the present invention is preferably characterized by the particle size (which is preferably referred to as average particle diameter of the particles of granulate of the present invention, as measured preferably by sieving) of less than 0.8 mm.

The present inventors have surprisingly found that the composition of the present invention, as defined herein, not only is effective in use in inhibition of crystallization and/or biofilm formation on indwelling urinary catheter, but also shows an optimal ratio of the components (which is herein understood as weight ratio or molar ratio) and allows to minimize potential side effects that would be associated with administration of potassium ions and/or magnesium ions. Increased dosage of potassium could lead to hyperkalaemia, an elevated level of potassium ions in blood, which, in certain cases, may cause palpitations, muscle pain, muscle weakness or numbness, or abnormal heart rhythm which can result in cardiac arrest or death. The risk of abnormal heart rhythm leading to cardiac arrest and potentially death is particularly apparent in a subject suffering from previous cardiological problems. As known to the skilled person, the daily dose of potassium (adult person) should not exceed 100 mEq, as higher doses may lead to cardiological complications.

Notwithstanding the cardiology-related side effects of potassium ions in the composition, it is noted that with increasing concentration of potassium in the solution, unpleasant metallic and/or bitter taste appears, which may be detrimental to patient's/subject's compliance when taking the composition of the present invention, in particular over an extended period of time (preferably referred to herein as at least once daily, preferably for more than 1 month, for more than 2 months, for more than 3 months, or for more than 6 months). Furthermore, the present inventors have surprisingly found that the composition of the present invention is characterized by solubility that warrants oral administration of the composition, and leads to increased patient compliance.

In turn, administration of higher amounts of magnesium salts is also not recommended as it may lead to side effects. The most common side effect reported that is associated with high doses of magnesium salt is diarrhoea, which is due to laxative effects of magnesium salts. It is herein assumed that daily dose of magnesium ions should not exceed 27 mEq.

Equivalent, referred to as Eq, is defined as the amount of a substance that reacts with (or is equivalent to) an amount of one mole of another substance in a given chemical reaction. Herein, as equivalents refer to amounts of magnesium ions, potassium ions and citrate ions, the amount of each ion as expressed in Eq is defined as its amount in moles multiplied by valency of this ion. For illustration purposes only, it is noted that one mole of magnesium ions corresponds to two Eq of magnesium ions, one mole of potassium ions corresponds to one Eq of potassium ions, and one mole of citrate ions (fully deprotonated) corresponds to three Eq of citrate ions.

The composition of the present invention may further comprise additional pharmaceutically acceptable excipients, including sweeteners, taste enhancers, antiadherents, binders, coatings, colouring agents, disintegrants, glidants, lubricants, and/or vehicles. Thus, in a further embodiment, the present invention relates to the composition as described herein, wherein the composition further comprises a pharmaceutically acceptable excipient.

The composition of the present invention is preferably to be administered orally to a subject, in particular to a patient in the need thereof. It is noted that, as it has been surprisingly found by the present inventors, the particular composition of the present invention, in particular the composition featuring the molar ratio of magnesium ions to potassium ions as described herein, or the weight contents of tripotassium citrate monohydrate and anhydrous trimagnesium citrate as described herein, is optimal for oral uptake of the composition of the present invention.

The composition of the present invention may be provided to a subject, in particular to a patient, as a single dose during the day, or in the course of several doses. Within the scope of the present invention it is preferred that a single dose of the composition comprises between 10 and 30 mEq of citrates. It has been surprisingly found by the present inventors that such a dosing regimen allows for improved compliance on the subject (i.e., patient) side, as any side effects related to the presence of counterions, herein potassium and magnesium, as described herein, are reduced to the acceptable level.

The single dose, as described herein, may be administered to a subject (i.e. to a patient) once or more times a day. Preferably, a single dose as described herein is administered to the subject once to twice a day. Such administration regime does not put excessive burden on the subject/patient and allows for optimal compliance. As understood herein, a daily dose of the composition of the present invention is preferably a sum of daily doses administered to a subject (to a patient) in the course of the day. Preferably, a daily dose of the composition comprises between 10 and 60 mEq of citrates.

It has been surprisingly found by the present inventors that administration of the composition of the present invention, as defined herein, reduces the risk of obstruction of the indwelling urinary catheter. As described hereinabove, crystallization and/or biofilm formation on the indwelling urinary catheter may affect the flow of urine through the catheter and lead to its obstruction. As understood herein, inhibiting these processes reduces the related risk, and has a potential of preventing the obstruction of the indwelling urinary catheter.

As a result of administration of the present composition, the biofilm formation and/or crystallization on an indwelling urinary catheter is reduced and/or inhibited. Therefore, as encompassed with the invention, administration of the composition of the present invention allows application of the indwelling urinary catheter to a patient for a prolonged period of time, which may herein be understood as more than 4 weeks, more than 6 weeks, more than 8 weeks, more than 10 weeks, more than 12 weeks or even longer. Administration of the composition of the present invention over an extended period of time is particularly recommended for subjects/patients that require long-term catheterization.

It is further noted that when the composition of the present invention is administered to a subject, or to patient, in the need of long-term catheterization, the indwelling urinary catheter does not need to be exchanged as often as typically done in contemporary clinical practice. Thus, complications related to frequent exchange of the indwelling urinary catheter can be avoided. Thus, in again a further particular embodiment, the present invention relates to the composition as described herein, wherein administration of the composition reduces the risk of an injury of urethra mucosa as a result of exchange of the indwelling urinary catheter.

Further encompassed by the invention is an embodiment, wherein administration of the composition reduces the risk of a catheter-associated urinary tract infection. As discussed herein above, the presence of the indwelling urinary catheter constitutes structural abnormality in the urinary tract which may lead to an increased propensity of the urinary tract to become infected. Furthermore, it is noted that presence of biofilm, as a microenvironment promoting microbial presence and/or growth, may further promote infections in the urinary tract. Such infections which are associated with the presence of an indwelling urinary catheter may also be referred to by a skilled person as catheter-associated urinary tract infections (abbreviated as CAUTIs) and may be cause by any microorganism capable by growing in urinary tract. Such a microorganism may also be referred to as uropathogenic microorganism. The non-exhaustive list of microorganisms that may cause a catheter-associated urinary tract infection includes *Escherichia coli, Pseudomonas aeruginosa, Staphylococcus aureus, Klebsiella pneumoniae, Morganella morganii, Proteus mirabilis, Proteus vulgaris, Providentia rettgeri*, and yeasts. However, this list is not meant to be limiting. It is noted that for each day of the catheter remaining in situ, there is an increasing risk from 3% to 7% for an infection to appear. It is further noted that other types of catheters, including suprapubic catheter and pigtail catheter, are also associated with increased risk of contracting a catheter-associated urinary tract infection.

Several bacteria are present in the urinary tract, either as members of the normal body microbiome, or originating from external sources and contributing to infections. *E. coli* is primarily found in gastrointestinal tract, but due to proximity of the urethra to the anus, especially in female patients, it is a large contributor to the catheter associated urinary tract infections, in particular for users of intermittent catheter. In particular, strains of *E. coli* that cause urinary tract infections are referred to as uropathogenic *E. coli* strains.

Many uropathogenic bacteria produce urease which hydrolyses urea, increasing the pH of the urine and ultimately leading to precipitation of calcium and magnesium in the urine and formation of crystalline biofilm on indwelling urinary catheters. One example of such bacterial species is *Proteus mirabilis*, a member of Enterobacteriaceae family. *Proteus* species are widely distributed in the environment and opportunistic, and have been linked to several nosocomial infections throughout the body. Nosocomial is herein understood as related to hospital stay, typically starting within 72 hours of hospital admission. *P. mirabilis* is normally not associated with urinary tract infections in healthy persons with unobstructed urinary tracts. It can however colonize the urinary tract of individuals with structural or functional abnormalities, wherein catheterised patients, in particular those with an indwelling urinary catheter, are mostly at risk. *P. mirabilis* has been shown to display the greatest propensity to bind the surface of catheters and urological devices in general, presumably due to production of multiple adherence factors. Importantly, *P. mirabilis* produces urease, which hydrolyses urea, and is essential for crystalline biofilm formation in the urinary tract. Of note, *P. mirabilis* exhibits the highest production of urease out of all uropathogens, and the urease it produces is very reactive and can hydrolyse urea faster than ureases from other species.

The present invention further relates to the composition as described herein, wherein the catheter-associated urinary tract infection causes a crystalline biofilm deposition. Crystallization can be caused by presence in the urinary tract of by any bacterium that produces urease enzyme, or by infection of the urinary tract by any bacterium that produces urease enzyme. Beyond *Proteus mirabilis*, other species of *Proteus* genus, for example *Proteus vulgaris*, are known to have similar effects. There are further bacterial species beyond *Proteus* spp, that are capable of producing urease, for example *Providentia rettgeri*. All the species mentioned herein have been isolated from biofilms, in particular crystalline biofilms, formed in the urinary tract of patients. Thus, the present invention relates to the composition as described herein, wherein the inhibited crystallization and/or biofilm formation is caused by presence of *Proteus mirabilis, Proteus vulgaris*, or *Providentia rettgeri*, preferably of *Proteus mirabilis.*

A number of further bacterial species that do not form crystallized biofilms, as their urease output is considerably lower as that of *Proteus mirabilis* or other species referred to hereinabove, may form a biofilm that is not crystalline. These species include *Pseudomonas aeruginosa, Staphylococcus aureus, Klebsiella pneumoniae, Morganella morganii*, and *Providencia stuarii*. Furthermore, fungal species, including *Candida albicans* may also be involved in forming non-crystalline biofilms. It is noted that the list is not meant to be limiting and other microbial (in particular bacterial) species may also form a non-crystalline biofilm. Typically, the bacterial species as listed herein produce large amounts of a mucoid material. While typically such mucoid material does not (completely) block the catheter, it certainly affects the urine flow therethrough and thus is highly undesired. Therefore, preventing such biofilm formation is highly desired, as described herein. Thus, in again a further particular embodiment, the present invention relates to the composition as described herein, wherein the inhibited biofilm formation is caused by presence of *Pseudomonas aeruginosa, Staphylococcus aureus, Klebsiella pneumoniae, Escherichia coli, Citrobacter* spp. and/or *Candida albicans.*

The processes of biofilm formation and crystallization, as known to the skilled person, are closely interrelated. One may also refer to a process of crystalline biofilm formation. The present inventors have further surprisingly found that the composition of the present invention is effective against biofilm formation, crystallization and/or crystalline biofilm formation, Thus, it is noted that, in another embodiment, the present invention relates to use of the composition as described herein for inhibition of crystallization and/or biofilm formation on indwelling urinary catheter.

The present inventors have further surprisingly found that administration of the composition as described herein is effective in inhibiting crystallization in urinary tract. The crystallization as understood herein includes crystallization of calcium phosphate, magnesium phosphate, as well as calcium oxalate. It is understood herein that upon administration of citrates, calcium can be chelated by citrate instead of oxalate, reducing the risk of bladder stone formation. It is thus understood herein that the present invention further relates to the composition as described herein, wherein administration of the composition reduces the risk of bladder stone formation.

Preferably, the administration of the composition of the present invention to a subject is to begin substantially at the same time as the catheterization of said subject. More preferably, the administration of the composition of the present invention to a subject is to start not later than the catheterization of said subject. Substantially at the same time can preferably be understood as happening within 1 hour of each other, more preferably happening within 30 minutes of each other. The present inventors have demonstrated that the addition of the composition of the invention into urine leads to much better results in terms of inhibition of crystallization and/or biofilm formation on indwelling urinary catheters than administration thereafter, as shown in Example 2.

As further shown by the present inventors in Example 2, the composition of the present invention is particularly effective for inhibition of crystallization and/or biofilm formation on indwelling urinary catheters, wherein upon administration the concentration of citrate ions in urine is maintained at a particular level. Thus, preferably, the composition of the present invention is to be administered to a subject in a dose so that the concentration of citrate ions in urine of said subject reaches a concentration of at least 1 mmol/L, more preferably at least 2 mmol/L, even more preferably at least 3 mmol/L, even more preferably about 4 mmol/L, most preferably 4 mmol/L. It is to be understood that a physician will be in position to determine an optimal dosing regimen, based on the physical and/or clinical data of a particular subject, so that this condition is fulfilled.

In further embodiments, the present invention relates to use of the composition as described hereinabove for inhibition of crystallization and/or biofilm formation on indwelling urinary catheters. The invention further relates to methods of treatment, encompassing administration of the composition of the present invention as defined hereinabove to the person in need of, in particular to the person undergoing long term catheterization with an indwelling urinary catheter, for inhibition of crystallization and/or biofilm formation on indwelling urinary catheter.

Various modifications and variations of the invention will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be covered by the present invention.

The following examples are merely illustrative of the present invention and should not be construed to limit the scope of the invention which is defined by the appended claims.

EXAMPLES

Example 1: The Composition of the Present Invention Consisting of Only Two Salts The composition was obtained by mixing 1441.8 mg of tripotassium citrate monohydrate and 501.2 mg of anhydrous trimagnesium citrate. Both salts are of API quality and have been provided by Jungbunzlauer Ladenburg GmbH, Dr.-Albert-Reimann-Str. 18, DE-68526 Ladenburg. The composition is also referred to as Pro24c.

Example 2: Stenosis of Bladder Catheters Due to Urease-Induced Biofilm- and Crystallization-Formation with Subsequent Encrustation Measured by Throughflow Rates and its Inhibition by Pro24c (an In Vitro-Study)

Introduction

An in vitro-study was performed with Pro24c (medicinal product, composed of anhydrous trimagnesium citrate and tripotassium citrate monohydrate, see Example 1) in order to demonstrate that this medicinal product is able to reduce or to inhibit the urease-induced biofilm-formation and crystallization on bladder catheters.

The enzyme urease (in vivo produced by microorganisms or in synthetic form commercially available) leads to biofilm-formation and different phases (nucleation, growth, aggregation) of crystallization in the urine, and on catheters respectively. This process on/in catheters results in encrustation and loss of catheter patency (blockage).

In this in vitro-study the mentioned process was quantified by measurements of the time-periods required for the throughflow of a defined volume of water (also referred to as flow-times) through the catheters.

Design and Methods

For the study synthetic urine and urease (high-purity preparation of Jackbean, dissolved in 0.1 M TRIS giving an activity of 109.09 mmol $NH_3$ from urine/min per milliliter at 37° C.) were used. Four big sterile glass vessels (2 L) were filled each with 1.5 liters synthetic urine. The urine was adjusted to a pH of 5.5 (with 32% HCl). Glass vessel No. 1 served as control. Glass vessel No. 2 was prepared with 1 mmol/L of Pro24c and glass vessel No. 3 with 4 mmol/L of Pro24c, respectively. Afterwards the urease-solution (0.1 ml per 100 ml urine) was added into all vessels. In glass vessel No. 4 Pro24c (the higher concentration of 4 mmol/L) was added not before 72 h from the start of the experiment.

The glass vessels were placed on heatable magnetic stirrers at 37° C. During incubation, continuous slow stirring was provided by Teflon-coated stirring bars. At the same time when the urease-solution was added, in each glass vessel 40 bladder catheters (CH-14; 18 cm; PharmaPlast) were hanged, fixed on triangular meshes.

The duration of the study was set to a maximum of 14 days. The pH was controlled every day at the same time. At the time-points of 2, 4, 6, 8 and 10 days, out of each glass vessel 5 catheters were taken. With each catheter a measurement of the flow was performed. For this purpose, the catheter was fixed in a funnel and 150 ml water (correctly calibrated) were allowed to flow freely through the catheter (without added pressure, only according to the force of gravity). The time for this procedure (flow-time) was measured and recorded.

Results

The pH rose in each glass vessel from 5.5 to over a value of 8 after the first day and remained constantly on this level throughout the whole study-time. The results of the flow-times (in seconds)—mean values—that were recorded for the flow of 150 ml water through the catheters, are presented in Tab. 1 and FIG. 1.

In glass vessel No. 1 (control) the mean flow-time rose from 15.93 seconds (at 0 days time point) to 20.62 seconds at the time-point of 10 days. That is an increase of 29.4%.

In the glass vessels No. 2 and No. 3 (containing 1 mmol/L and 4 mmol/L Pro24c, respectively) the corresponding mean values of flow-time increased by 7% and decreased by 3.4%, respectively.

In glass vessel No. 4 (Pro24c added only after 72 h) the increase of the mean flow-time was 42.5% at time-point 8 days. (At time-point 10 days the result was not evaluable due to technical problems).

TABLE 1

Flow-times of 150 mL water for each condition given as mean values for 5 catheters per time point, as described hereinabove.

| | 0 days | 2 days | 4 days | 6 days | 8 days | 10 days |
|---|---|---|---|---|---|---|
| Control | 15.93 | 15.62 | 15.87 | 15.79 | 19.78 | 20.62 |
| 1 mmol | 15.89 | 15.82 | 15.41 | 15.44 | 16.20 | 17.00 |
| 4 mmol | 15.92 | 15.41 | 15.27 | 15.52 | 15.25 | 15.41 |
| 4 mmol + 72 h | 15.98 | 15.80 | 15.74 | 15.79 | 22.77 | n.e. |

These differences are striking and significant. Catheters hanging in untreated urine show over a time period of 10 days a clear tendency to develop crystallization and encrustation and consequently a loss of patency. Pro24c in a concentration of 4 mmol/L inhibits this blockage. As seen from the experiment in glass vessel No. 4 it is reasonable to give Pro24c right at the beginning of catheterization (i.e., when a catheter is placed in a patient) and not after a certain lag time.

CONCLUSION

It is known from the literature that in vitro-studies, as the one described above, are able to demonstrate and to verify the value of a medicinal product in preventing biofilm-formation, crystallizations and encrustations on bladder catheters and therefore to inhibit blockages of these catheters with the corresponding complications. Pro24c is a medicinal product for prevention of biofilm-formation and crystallization on indwelling urinary catheters.

Further aspects and/or embodiments of the invention are disclosed in the following numbered items:

1. A composition comprising magnesium, potassium and citrate for use in the inhibition of crystallization and/or biofilm formation on an indwelling urinary catheter.
2. The composition for use of item 1, wherein magnesium, potassium and/or citrate are present as ion(s).
3. The composition for use of item 2, wherein the molar ratio of potassium ions to magnesium ions in the composition is between 3.2:1 and 5.5:1.
4. The composition for use of item 2 or 3, wherein the molar ratio of potassium ions to magnesium ions to citrate ions in the composition is about 4:1:2, preferably 4:1:2.
5. The composition for use of any one of items 1 to 4, wherein the composition comprises trimagnesium citrate, preferably anhydrous trimagnesium citrate, and/or wherein the composition comprises tripotassium citrate, preferably tripotassium citrate monohydrate.
6. The composition for use of item 5, wherein the tripotassium citrate monohydrate constitutes 70-80 weight % of the citrate salts in the composition, and wherein anhydrous trimagnesium citrate constitutes 20-30 weight % of the citrate salts in the composition.

7. The composition for use of item 6, wherein the tripotassium citrate monohydrate constitutes 74.2 weight % of the citrate salts in the composition, and wherein anhydrous trimagnesium citrate constitutes 25.8 weight % of the citrate salts in the composition.
8. The composition for use of item 6 or 7, wherein the composition consists of 74.2 weight % tripotassium citrate monohydrate and of 25.8 weight % anhydrous trimagnesium citrate.
9. The composition for use of any one of items 1 to 8, wherein upon dissolution of the composition in water the pH is between 6.0 and 9.0.
10. The composition for use of any one of items 1 to 9, wherein the composition is to be administered orally.
11. The composition for use of any one of items 1 to 7, 9 or 10, wherein the composition further comprises a pharmaceutically acceptable excipient.
12. The composition for use of any one of items 1 to 11, wherein a single dose of the composition comprises between 10 and 30 mEq of citrates.
13. The composition for use of any one of items 1 to 12, wherein a daily dose of the composition comprises between 10 and 60 mEq of citrates.
14. The composition for use of any one of items 1 to 13, wherein administration of the composition reduces the risk of obstruction of an indwelling urinary catheter.
15. The composition for use of any one of items 1 to 14, wherein administration of the composition allows application of the indwelling urinary catheter for a prolonged period of time.
16. The composition for use of any one of items 1 to 15, wherein administration of the composition reduces the risk of a catheter-associated urinary tract infection.
17. The composition for use of any one of items 1 to 16, wherein the inhibited crystallization and/or biofilm formation is caused by presence of *Proteus mirabilis, Proteus vulgaris*, and/or *Providentia rettgeri*, preferably of *Proteus mirabilis.*
18. The composition for use of any one of items 1 to 16, wherein the inhibited biofilm formation is caused by presence of *Pseudomonas aeruginosa, Staphylococcus aureus, Klebsiella pneumoniae, Escherichia coli, Citrobacter* spp. and/or yeasts, in particular *Candida albicans.*
19. The composition for use of any one of items 1 to 18, wherein administration of the composition reduces the risk of bladder stone formation.
20. The composition for use of any one of items 1 to 19, wherein administration of the composition reduces the risk of an injury to urethra mucosa as a result of exchange of the indwelling urinary catheter.
21. Use of the composition as described in any one of items 1 to 9 for inhibition of crystallization and/or biofilm formation on an indwelling urinary catheter.

Further aspects and/or embodiments of the invention are disclosed in the following numbered paragraphs:

1. A composition comprising magnesium, potassium and citrate for use in the inhibition of crystallization and/or biofilm formation on an indwelling urinary catheter, wherein magnesium, potassium and citrate are present as ion(s).
2. The composition for use of paragraph 1, wherein the molar ratio of potassium ions to magnesium ions in the composition is between 3.2:1 and 5.5:1.
3. The composition for use of paragraph 2, wherein the molar ratio of potassium ions to magnesium ions to citrate ions in the composition is about 4:1:2, preferably 4:1:2.
4. The composition for use of any one of paragraphs 1 to 3, wherein the composition comprises trimagnesium citrate, preferably anhydrous trimagnesium citrate, and/or wherein the composition comprises tripotassium citrate, preferably tripotassium citrate monohydrate.
5. The composition for use of paragraph 4, wherein the tripotassium citrate monohydrate constitutes 70-80 weight % of the citrate salts in the composition, and wherein anhydrous trimagnesium citrate constitutes 20-30 weight % of the citrate salts in the composition.
6. The composition for use of paragraph 5, wherein the tripotassium citrate monohydrate constitutes 74.2 weight % of the citrate salts in the composition, and wherein anhydrous trimagnesium citrate constitutes 25.8 weight % of the citrate salts in the composition.
7. The composition for use of paragraph 5 or 6, wherein the composition consists of 74.2 weight % tripotassium citrate monohydrate and of 25.8 weight % anhydrous trimagnesium citrate.
8. The composition for use of any one of paragraphs 1 to 7, wherein upon dissolution of the composition in water the pH is between 6.0 and 9.0, and/or wherein the composition is to be administered orally, and/or wherein the composition further comprises a pharmaceutically acceptable excipient.
9. The composition for use of any one of paragraphs 1 to 8, wherein a single dose of the composition comprises between 10 and 30 mEq of citrates, and/or wherein a daily dose of the composition comprises between 10 and 60 mEq of citrates.
10. The composition for use of any one of paragraphs 1 to 9, wherein administration of the composition reduces the risk of obstruction of an indwelling urinary catheter, and/or wherein administration of the composition allows application of the indwelling urinary catheter for a prolonged period of time.
11. The composition for use of any one of paragraphs 1 to 10, wherein administration of the composition reduces the risk of a catheter-associated urinary tract infection.
12. The composition for use of any one of paragraphs 1 to 11, wherein the inhibited crystallization and/or biofilm formation is caused by presence of *Proteus mirabilis, Proteus vulgaris*, and/or *Providentia rettgeri*, preferably of *Proteus mirabilis*, and/or wherein the inhibited biofilm formation is caused by presence of *Pseudomonas aeruginosa, Staphylococcus aureus, Klebsiella pneumoniae, Escherichia coli, Citrobacter* spp. and/or yeasts, in particular *Candida albicans.*
13. The composition for use of any one of paragraphs 1 to 12, wherein administration of the composition reduces the risk of bladder stone formation.
14. The composition for use of any one of paragraphs 1 to 13, wherein administration of the composition reduces the risk of an injury of urethra mucosa as a result of exchange of the indwelling urinary catheter.
15. Use of the composition as described in any one of paragraphs 1 to 8 for inhibition of crystallization and/or biofilm formation on an indwelling urinary catheter.

The invention claimed is:

1. A method for inhibiting crystallization and/or biofilm formation on an indwelling urinary catheter, which comprises administering a composition that comprises magnesium, potassium and citrate ions, to a subject, wherein said administration begins within 1 hour of the catheterization of said subject; and wherein the composition comprises tripotassium citrate monohydrate and anhydrous trimagnesium citrate;

wherein the molar ratio of potassium ions to magnesium ions to citrate ions in the composition is 4:1:2; and wherein the tripotassium citrate monohydrate constitutes 70-80 weight % of the citrate salts in the composition and the anhydrous trimagnesium citrate constitutes 20-30 weight % of the citrate salts in the composition.

2. The method of claim 1, wherein the tripotassium citrate monohydrate constitutes 74.2 weight % of the citrate salts in the composition, and wherein anhydrous trimagnesium citrate constitutes 25.8 weight % of the citrate salts in the composition.

3. The method of claim 2, wherein the composition consists of 74.2 weight % tripotassium citrate monohydrate and of 25.8 weight % anhydrous trimagnesium citrate.

4. The method of claim 1, wherein the composition is administered orally to said subject.

5. The method of claim 4, wherein said composition is in solid form and said oral administration comprises dissolving the composition in water to obtain a pH between 6.0 and 9.0.

6. The method of claim 1, wherein the composition further comprises a pharmaceutically acceptable excipient.

7. The method of claim 1, wherein a single dose of the composition comprises between 10 and 30 mEq of citrates, and/or wherein a daily dose of the composition comprises between 10 and 60 mEq of citrates.

8. The method of claim 1, wherein the administration further comprises administering the composition once or twice per day to the subject.

9. The method of claim 1, wherein the administration of the composition reduces the risk of obstruction of an indwelling urinary catheter, and/or wherein administration of the composition allows application of the indwelling urinary catheter for a prolonged period of time.

10. The method of claim 1, wherein the administration of the composition reduces the risk of a catheter-associated urinary tract infection.

11. The method of claim 1, wherein the crystallization and/or biofilm formation that is inhibited is caused by the presence of *Proteus mirabilis, Proteus vulgaris, Providentia rettgeri, Pseudomonas aeruginosa, Staphylococcus aureus, Klebsiella pneumoniae, Escherichia coli, Citrobacter* spp. and/or yeasts.

12. The method of claim 1, wherein the administration of the composition reduces the risk of bladder stone formation.

13. The method of claim 1, wherein the administration of the composition reduces the risk of an injury of urethra mucosa as a result of exchange of the indwelling urinary catheter.

14. The method of claim 1, wherein the administration of the composition to the subject results in a concentration of citrate ions in urine of said subject of at least 1 mmol/L.

15. The method according to claim 14, wherein the administration of the composition results in a citrate ion concentration in said subject of at least 2 mmol/L.

16. The method according to claim 15, wherein said administration results in a citrate ion concentration in said subject of at least 3 mmol/L.

17. The method according to claim 14, wherein said administration results in a citrate ion concentration in said subject of about 4 mmol/L.

* * * * *